US00PP27595P3

(12) United States Plant Patent
Travers

(10) Patent No.: US PP27,595 P3
(45) Date of Patent: Jan. 24, 2017

(54) ***CLEMATIS* PLANT NAMED 'TRA73'**

(50) Latin Name: ***Clematis* hybrid**
Varietal Denomination: TRA73

(71) Applicant: Bernard Travers, Saint Cyr en Val (FR)

(72) Inventor: Bernard Travers, Saint Cyr en Val (FR)

( * ) Notice: Subject to any disclaimer, the term of this patent is extended or adjusted under 35 U.S.C. 154(b) by 88 days.

(21) Appl. No.: 14/544,081

(22) Filed: Nov. 24, 2014

(65) Prior Publication Data

US 2016/0150708 P1 May 26, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

UPOV—International Union for the Protection of New Varieties of Plants, PLUTO:Plant Variety Database; Apr. 14, 2016; citation for 'TRA73' (1 pg total).*

* cited by examiner

*Primary Examiner* — Susan McCormick Ewoldt
(74) *Attorney, Agent, or Firm* — Cassandra Bright

(57) ABSTRACT

A new and distinct *Clematis* hybrid named 'is disclosed, characterized by unique magenta flowers with convex tepals. Flowers occur from the base of the plant to the top. Flowering season is continuous from April until September. The new cultivar is a *Clematis* typically suited for ornamental container and landscape use.

1 Drawing Sheet

Latin name of the genus and species: *Clematis* hybrid.
Variety denomination: 'TRA73'.

BACKGROUND OF THE INVENTION

The new cultivar is the result of a breeding program, with the objective to develop new varieties of *Clematis* with strong growth and interesting flowers for commercial purposes. The new variety was discovered as a single plant among a group of seedlings of unknown parentage observed by the inventor, Bernard Travers. The discovery was made during 1999. Discovery was made at a commercial nursery in Orleans, France.

After selecting and isolating the new cultivar, asexual reproduction of the new cultivar 'TRA73' was first performed at a commercial nursery in St. Jean Le Blanc by vegetative cuttings during 2002. The inventor maintained the original plant, and observed the clones for several years, to establish stability of the characteristics. 'TRA73' has since produced multiple generations and has shown that the unique features of this cultivar are stable and reproduced true to type. Public access to plant material first occurred during early Spring of 2014. Before this time, plant material was under the control of the inventor, or those directly authorized by the inventor and no enabling access to plant material occurred. This variety has been applied for Plant Breeder's Right's Protection in the EU, with CPVO application number 2013/1736. A copy of the technical questionnaire is included with the mailing of this application. A grant has not yet issued, and technical exam process has not been completed. Neither the application, nor any other publication resulted in an enabling disclosure of 'TRA73'.

SUMMARY OF THE INVENTION

The cultivar 'TRA73' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TRA73'. These characteristics in combination distinguish 'TRA73' as a new and distinct *Clematis* cultivar:

1. Flowers occurring from base to top of plant
2. Many axillary flowers buds
3. Magenta flowers
4. Abundant bright yellow stamens
5. Long flowering season, with new flowers forming from Spring through Summer
6. Convex aspect of tepals.

PARENTAL COMPARISON

Parent varieties are unknown, the breeder is unable to supply records of the crossings.

COMMERCIAL COMPARISON

Plants of the new cultivar 'TRA73' can be compared to the known commercial variety *Clematis* hybrid 'Ville de Lyon' unpatented. The *Clematis* varieties are similar in most horticultural characteristics, however 'TRA73' differs from 'Ville de Lyon' in the following:

1. Plants of 'TRA73' rebloom from Spring through Summer, whereas plants of 'Ville de Lyon' have a single of flush of flowers.
2. 'TRA73' has uniquely convex tepals, not found on this comparator.
3. Different tepal shape.

Plants of the new cultivar 'TRA73' can be compared to the known commercial variety *Clematis* 'Ernest Markam', unpatented. The *Clematis* varieties are similar in most horticultural characteristics. 'TRA73' differs from the comparator in the following:

1. Plants of 'TRA73' reach a mature height between 200 and 300 cm, whereas mature plants of this comparator grow to 300-400 cm.
2. 'TRA73' produces tepals with acute to apiculate aspices, whereas the apex of tepals of this comparator are characteristically rounded.
3. Tepals of the comparator variety are more overlapping.

BRIEF DESCRIPTION OF THE PHOTOGRAPH

The accompanying photograph in FIG. 1 illustrates in full color a typical flowers and foliage of 'TRA73'. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'TRA73' plants grown outdoors in Saint Cyr en Val, France. The growing temperature ranged from approximately −2° C. to 25° C. at night to 8° C. to 33° C. during the day. No artificial light, photoperiodic treatments or chemical treatments were given to the plants. Measurements and numerical values represent averages of typical flowering types.

Botanical classification: *Clematis* hybrid 'TRA73'.

Age of the plant described: Approximately 8 months.

PROPAGATION

Typical method: Vegetative cuttings.

Time to initiate rooting: Approximately 20 days at 21° C. or higher.

Time to produce a rooted plantlet: Approximately 40 days at 20° C. or higher.

Root description: Fine, fibrous.

PLANT

Growth habit: Climbing vine.

Height: Approximately 250 cm.

Plant spread: Approximately 100 cm.

Growth rate: Moderate to rapid. During active growing season in Spring, approximately 100 cm per month.

Branching characteristics: One main stem.

Length of main stem: Approximately 200 cm.

Diameter of main stem: Approximately 0.2 to 0.5 cm.

Main stem color: Near RHS Greyed-Purple 183A.

Main stem texture: Glabrous.

Internode length: Approximate range 5 cm to 12 cm.

Strength: Strong, flexible, semi-woody.

FOLIAGE

*Arrangement.*—Opposite, mostly compound trifoliate occasionally single.

*Overall leaf length.*—Approximately 15 cm long.

*Overall leaf diameter.*—Approximately 9 cm.

*Leaflets.*—Average length: Approximately 5.7 cm. Average width: Approximately 3.1 cm. Shape of blade: Narrow deltate. Apex: Acute. Base: Cordate to obtuse.

*Attachment.*—Stalked, twining leaf petiole.

*Margin.*—Entire.

*Texture of upper surface.*—Smooth with distinctly hirsute veins.

*Texture of lower surface.*—Rugose, slightly pubescent toward margin.

*Color.*—Young foliage upper side: Near RHS Green 143A. Young foliage under side: Near RHS Yellow-Green 144A. Mature foliage upper side: Near RHS Green 137C. Mature foliage under side: Near RHS Green 143B.

*Venation.*—Type: Pinnate. Venation color upper side: Near RHS Yellow-Green 144A. Venation color under side: Near RHS Yellow-Green 144A.

Petiole:

*Length.*—Range from 1.2 to 2.2 cm.

*Diameter.*—Approximately 0.1 to 0.3 cm.

*Texture.*—Hirsute.

*Color.*—Near RHS Green 137C, with Greyed-Purple 183D.

FLOWER

Bloom period:

*Natural season.*—Continuous flowering begins April or May and continues through September.

Inflorescence type and habit: Axillary occurring; 1 to 3 flowers, facing outward.

Rate of flower opening: Approximately 7 days from bud to fully opened flower.

Flower longevity on plant: Approximately 8 to 12 days, after fully opened. Self-cleaning.

Flower fragrance: None.

Inflorescence size:

*Diameter.*—Average 8.0 to 12.0 cm.

*Depth.*—Average 6.8 cm.

Corolla:

*Tepal arrangement.*—Single whorl, slightly overlapping.

*Quantity.*—6 per flower.

*Shape.*—Deltoid.

*Margin.*—Very slightly crenate.

*Aspect.*—Convex.

*Apex.*—Apiculate.

*Base.*—Truncate.

*Texture.*—Smooth, velvety upper and lower surfaces.

*Length.*—Average Range 2.7 to 5.9 cm.

*Width.*—Average 2.0 cm.

Color:

*Tepals.*—When opening: Upper surface: Near RHS Red-Purple 59C. Lower surface: Near RHS Red-Purple 59B. Fully opened: Upper surface: Near RHS Red-Purple 64B, some streaks near Red-Purple 68B. Lower surface: Near RHS Red-Purple 67A.

*Ageing.*—Upper surface: Near RHS Red-Purple 67B. Lower surface: Near RHS Red-Purple 67A.

Bud:

*Shape.*—Elongated sphere.

*Length.*—Approximately 15 cm.

*Diameter*.—Approximately 7.6 cm.
*Color*.—Near RHS Red-Purple 61A.

Pedicels:
*Length*.—Average range 5 to 10 cm.
*Width*.—Approximately 0.4 cm.
*Angle*.—Average 45° to 80°.
*Strength*.—Flexible.
*Color*.—Near RHS Green 137C flushed Greyed-Purple 183D.

REPRODUCTIVE ORGANS

Stamens:
*Number*.—Average 140 per flower.
*Anther length*.—Approximately 0.4 cm.
*Anther color*.—Near RHS Yellow 10A.
*Anther shape*.—Oblong.
*Filament length*.—Approximately 1.4.
*Filament color*.—Near RHS Yellow 4A.
*Pollen quantity*.—Moderate.
*Pollen color*.—Yellow-Orange 18A.

Pistil:
*Length*.—Approximately 2.4 cm.
*Style length*.—Approximately 1.1 cm.
*Stigma*.—Shape: Fine irregular hairs. Color: Near RHS Green-White 157B.

OTHER CHARACTERISTICS

Seeds: Seed production not observed.

Disease/pest resistance: Neither resistance nor susceptibility to normal diseases and pests of *Clematis* has been observed.

Temperature tolerance: Tolerates temperatures from approximately −20° C. to 45° C.

What is claimed is:

1. A new and distinct cultivar of *Clematis* hybrid plant named 'TRA73' as herein illustrated and described.

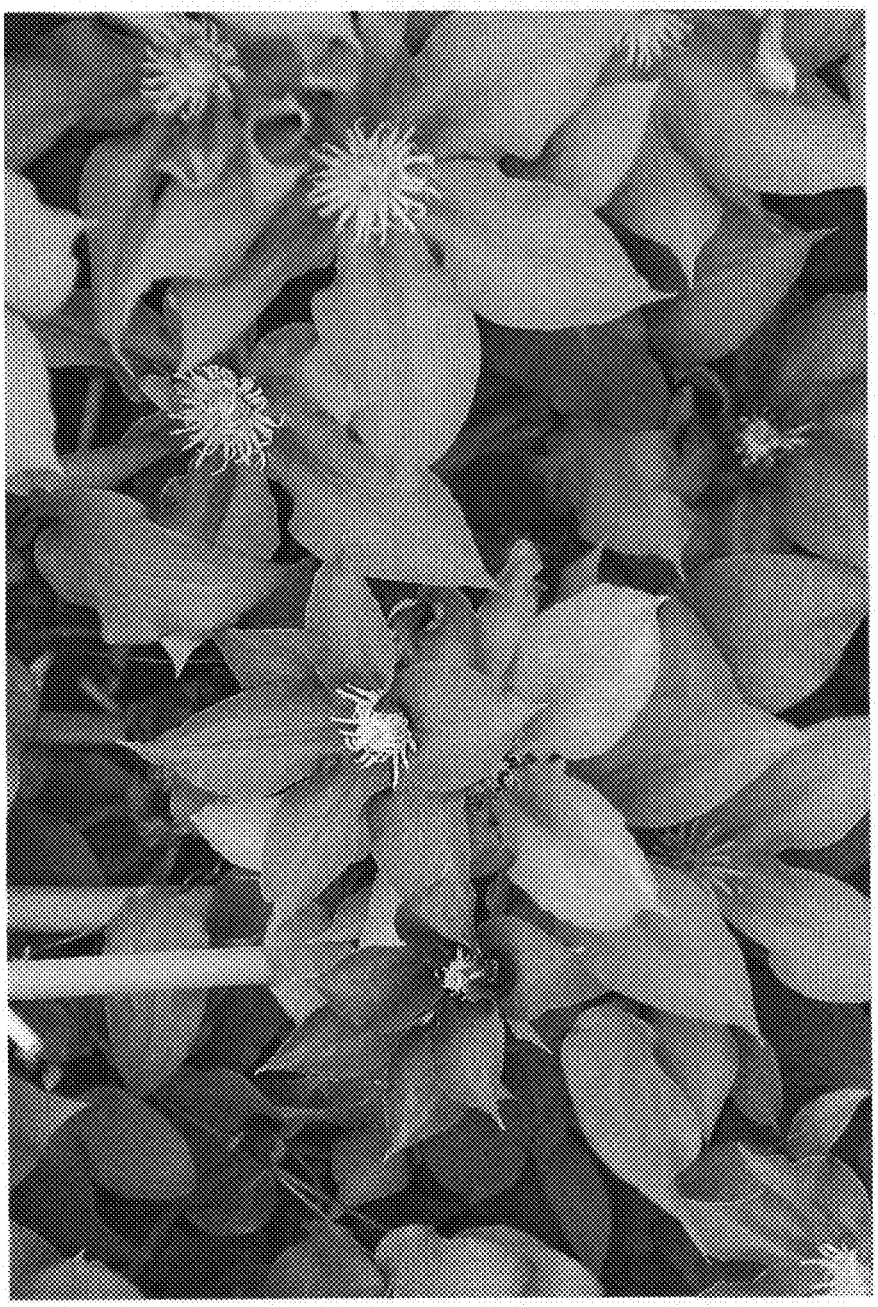

* * * * *